(12) United States Patent
Liu et al.

(10) Patent No.: US 11,940,361 B2
(45) Date of Patent: Mar. 26, 2024

(54) OPEN WATER ANALYSIS SYSTEM, RELATED METHODS, AND TWO-STAGE VORTEX FILTER

(71) Applicants: Shiwei Liu, Lehi, UT (US); Xiaoge Cheng, Beijing (CN); Tianye Wang, Halifax (CA); Ben Hatfield, Halifax (CA); Fred Lu, Halifax (CA)

(72) Inventors: Shiwei Liu, Lehi, UT (US); Xiaoge Cheng, Beijing (CN); Tianye Wang, Halifax (CA); Ben Hatfield, Halifax (CA); Fred Lu, Halifax (CA)

(*) Notice: Subject to any disclaimer, the term of this patent is extended or adjusted under 35 U.S.C. 154(b) by 119 days.

(21) Appl. No.: 17/459,281

(22) Filed: Aug. 27, 2021

(65) Prior Publication Data

US 2022/0136940 A1    May 5, 2022

Related U.S. Application Data

(60) Provisional application No. 63/079,978, filed on Sep. 17, 2020.

(51) Int. Cl.
| | | |
|---|---|---|
| *G01N 1/40* | (2006.01) | |
| *G01N 1/12* | (2006.01) | |
| *G01N 33/18* | (2006.01) | |
| *G06V 10/764* | (2022.01) | |
| *G01N 15/06* | (2006.01) | |

(52) U.S. Cl.
CPC ............ *G01N 1/4077* (2013.01); *G01N 1/12* (2013.01); *G01N 33/18* (2013.01); *G06V 10/764* (2022.01); *G01N 2001/4088* (2013.01); *G01N 2015/0693* (2013.01)

(58) Field of Classification Search
CPC ........ G01N 1/4077; G01N 1/12; G01N 33/18; G01N 2001/4088; G01N 2015/0693; G01N 2015/0294; G01N 2015/1445; G01N 2015/1454; G01N 15/1429; G01N 15/1434; G01N 15/1459; G01N 2015/149; G01N 2015/1493; G01N 2015/1497; G01N 15/0227; G01N 2001/021; G01N 1/14; G01N 2001/1006; G01N 1/10; G01N 33/1826; G01N 33/1866; G06V 10/764; G01S 15/88; G01S 15/89
USPC .... 73/232, 53.1, 61.41, 61.43, 61.71, 64.56, 73/170.29, 170.33, 863.21, 863.23, 73/864.34, 865.5; 356/440, 441, 442; 348/61
See application file for complete search history.

(56) References Cited

U.S. PATENT DOCUMENTS 9,689,787 B2 * 6/2017 Hallset ............... G01N 15/1463

FOREIGN PATENT DOCUMENTS

| CN | 108414284 A | * | 8/2018 | |
|---|---|---|---|---|
| CN | 108627366 A | * | 10/2018 | ............... G01N 1/14 |

(Continued)

*Primary Examiner* — Robert R Raevis

(57) ABSTRACT

The present disclosure provides an integrated collection, filtration, and analysis system which is configured to automatically collect fluid samples from a surrounding open water environment, isolate floating particles of a target size range, and perform analysis on the collected particles in-situ. The particles may also be filtered by one or more parameters other than size, and also provided herein is a two-stage vortex filter specially adapted to isolate floating particles of a desired density range from a fluid.

13 Claims, 9 Drawing Sheets

(56) References Cited

FOREIGN PATENT DOCUMENTS

| CN | 108663235 A | * | 10/2018 | ............. B63B 35/00 |
| CN | 109506984 A | * | 3/2019 | ............... G01N 1/14 |

* cited by examiner

OPEN WATER ANALYSIS SYSTEM, RELATED METHODS, AND TWO-STAGE VORTEX FILTER

CROSS-REFERENCE TO RELATED APPLICATIONS

The present application claims the benefit and priority of U.S. provisional application No. 63/079,978, filed 17 Sep. 2020 and of Canadian National application no. 3,091,337, filed 27 Aug. 2020, both of which are incorporated by reference.

FIELD OF INVENTION

The present invention relates generally to the fields of sample collection, isolation, and analysis, and more specifically to methods and related systems for analyzing and identifying particles of a target size range in a water sample.

BACKGROUND

Traditionally, analysis of particulates from open water samples comprised two distinctly separate phases. First, a collection phase in which, through manual sampling techniques, the target objects are collected from an open system, sorted, and transported to a separate and possibly distant laboratory specialized for such work. Subsequently, a second stage process requires a laboratory to extensively pre-process and filter the target objects from other objects collected with the sample before conducting analysis.

Such solutions are error-prone and limited in terms of efficiency, coverage, and scope of analysis. For instance, determining accurate co-ordinates for object concentrations in an area would prove challenging for several thousand individual objects if done manually. Furthermore, it is expensive to have to repeatedly transport samples back an forth form an open water environment to a laboratory.

It is within this context that the present invention is provided.

SUMMARY

The present disclosure provides an integrated collection, filtration, and analysis system which is configured to automatically collect fluid samples from a surrounding open water environment, isolate floating particles of a target size range, and perform analysis on the collected particles in-situ. The particles may also be filtered by one or more parameters other than size, and also provided herein is a two-stage vortex filter specially adapted to isolate floating particles of a desired density range from a fluid.

The integrated and automatic nature of the disclosed system greatly reduces the necessity for human involvement in operations such as microplastic pollution surveying, and the specially adapted vortex filter allows for a much greater precision of particle isolation from fluids containing suspended objects of interest.

Thus, according to one aspect of the present disclosure there is provided a system for collecting and analysing samples from an open water environment, the system comprising: a collection module configured to float within and receive water samples from a surrounding open water environment, the collection module comprising one or more filters for collecting objects of a target size range from the water samples; a filtration module comprising a filter configured to separate the collected objects according to a predetermined parameter and comprising outputs for the filtered and unfiltered objects; and an analyzation module comprising an imaging device and a processing device, the analyzation module configured to image the unfiltered objects from the filtration module to determine one or more characteristics of parameters of the unfiltered objects.

In some embodiments, the analyzation module comprising a translucent tube configured to pass the unfiltered objects through a scanning area of the image capture device.

In some embodiments, the filtration n module further comprises a sorting assembly configured to receive an output of the filter and an output of the analyzation module.

Furthermore, the sorting assembly may comprise one or more storage containers and one or more valves for directing the received filtered and unfiltered objects into the storage containers.

The unfiltered objects may be sorted according to one or more parameters or characteristics determined by the analyzation module.

In some embodiments, the image capture device is configured to generate 3D volumetric data for the unfiltered objects.

In some embodiments, the processing device is configured to classify and/or identify the unfiltered objects based on the image data captured by the image capture device.

Furthermore, the processing device may comprise a machine learning algorithm for classifying or identifying the unfiltered objects based on the captured image data.

In some embodiments, the system comprises an assembly of pumps and valves for directing the captured objects through the system.

In some embodiments, the collection module comprises a mesh filter at an input aperture for preventing objects above a certain size from entering the filter.

The collection module may comprise a trawl net between the mesh filter and a collection box for receiving the objects, the trawl filter having a mesh size chosen to allow objects below a certain size to escape the collection module.

In some embodiments, the collection module is provided with one or more buoyant stabilisers for maintaining a desired depth and/or orientation of the collection module.

In some embodiments, filter of the filtration module is a vortex filter configured to filter the objects by density.

According to another aspect of the present disclosure, there is provided a two-stage vortex filter configured to perform first and second sorting of particulate matter suspended in a fluid input to isolate one or more objects of a desired density range, the filter comprising: a first stage filter, comprising a container having a cylindrical section of a first diameter formed of a curved wall and a closed end, with a first fluid output disposed in the centre of the first end, and a tapered tunnel section having a proximal end connected to the cylindrical section and a distal tapered end comprising a second a fluid output, wherein the curved wall of the cylindrical section further comprises a fluid input of the vortex filter, the fluid input being aligned with the curved wall.

The two stage vortex filter further comprises a plurality of second-stage filters, each second stage filter comprising a container having a cylindrical section of a second diameter formed of a curved wall and a closed end, with a first fluid output disposed in the centre of the first end, and a tapered tunnel section having a proximal end connected to the cylindrical section and a distal tapered end comprising a second a fluid output, wherein the curved wall of the cylindrical section further comprises a fluid input connected to the second output of the first stage filter, the fluid input being aligned with the curved wall.

A density range of objects to be separated by the vortex filter is determined by the ratio of the first diameter and the second diameter and by the velocity of fluid received through the fluid input of the first stage filter.

In further aspects of the present disclosure, a method is provided, comprising the steps of: collecting a sample of fluid, the sample comprising a plurality of a defined target objects; removing objects from the sample of fluid that are larger than a threshold size; pumping the sample of fluid containing unfiltered objects through a substantially translucent conduit; capturing images of the unfiltered objects as they pass through the conduit, wherein a resolution of the image is sufficient to determine the size of the particles; and applying a trained machine learning system to the images to determine one or more properties of the unfiltered particles.

In some embodiments of the method, the image capture device can be either sonar or optical.

In some embodiments of the method, the images may comprise a video.

In some embodiments of the method, the machine learning system is a neural network.

Furthermore, the machine learning system may be configured to determine a property of the unfiltered objects, the property selected from the group consisting of a texture, a size, a color, or a shape of the unfiltered objects.

In some embodiments of the method, the method comprises generating a distribution chart of the property of the target objects.

In some embodiments of the method, the method comprises collecting properties of the unfiltered objects in a database of properties.

Furthermore, the method may also involve uploading the collected properties to a remote computing device for dissemination.

In some embodiments of the method, the method comprises training the machine learning system using a predetermined classification.

According to another aspect of the present disclosure, a method is provided comprising the steps of: collecting fluid comprising a plurality of particles; removing particles from the fluid that are larger than a threshold size; collecting unfiltered particles in the fluid using a trawl net; in response to collecting a threshold amount of unfiltered particles, combining the unfiltered particles in a pre-determined amount of fluid to yield a predetermined density of unfiltered particles in a sample fluid; pumping the sample fluid through a substantially translucent conduit; capturing three-dimensional image data of the unfiltered particles using a holographic microscope as they pass through a segment of the tube, wherein a speed of images is sufficient to capture each of the unfiltered particles as they pass through the tube; and applying a trained machine learning system to the images to determine one or more properties of the unfiltered particles.

In some embodiments of the method, before pumping the sample fluid through the tube, pumping the sample fluid through a plurality of vortex filters to remove particles from the sample of fluid that are below a threshold density.

In some embodiments of the method, the method comprises increasing a speed of the pumping in response to a density of unfiltered particles at the segment of the tube being above a threshold value.

In some embodiments of the method, the method comprises decreasing a speed of the pumping in response to a density of unfiltered particles at the segment of the tube being below a threshold value.

In some embodiments of the method, the method comprises depositing the sample of fluid in a container associated with a location of the collected fluid determined, the location determined using a GPS.

In some embodiments of the method, the method comprises associating the one or more properties of the unfiltered particles with a certain product by comparing the unfiltered particles to particles used by the product.

BRIEF DESCRIPTION OF THE DRAWINGS

Various embodiments of the invention are disclosed in the following detailed description and accompanying drawings.

Figure 1:
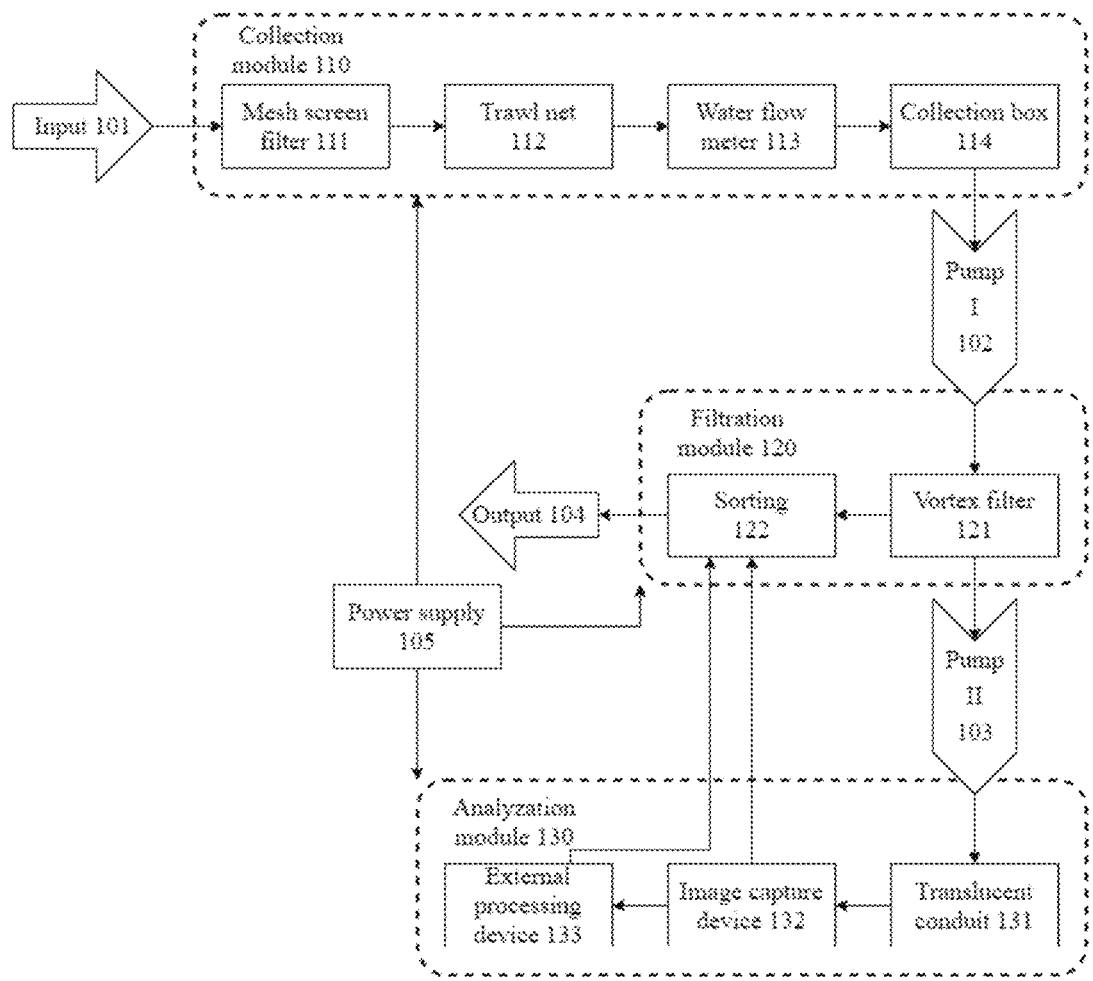
FIG. 1 is a block diagram illustrating a collection, filtering, and analysis pipeline, according to some example embodiments.

Common reference numerals are used throughout the figures and the detailed description to indicate like elements. One skilled in the art will readily recognize that the above figures are examples and that other architectures, modes of operation, orders of operation, and elements/functions can be provided and implemented without departing from the characteristics and features of the invention, as set forth in the claims.

DETAILED DESCRIPTION AND PREFERRED EMBODIMENT

The following is a detailed description of exemplary embodiments to illustrate the principles of the invention. The embodiments are provided to illustrate aspects of the invention, but the invention is not limited to any embodiment. The scope of the invention encompasses numerous alternatives, modifications and equivalent; it is limited only by the claims.

Numerous specific details are set forth in the following description in order to provide a thorough understanding of the invention. However, the invention may be practiced according to the claims without some or all of these specific details. For the purpose of clarity, technical material that is known in the technical fields related to the invention has not been described in detail so that the invention is not unnecessarily obscured.

The terminology used herein is for the purpose of describing particular embodiments only and is not intended to be limiting of the invention. As used herein, the term "and/or" includes any combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

The present disclosure provides an integrated open water analysis system comprising collection and filtration apparatus, and related sensor and analyzation system enabling automated concentration, collection, filtration, sorting, and analysis of defined target objects collected from open systems. Related methods and a specially adapted vortex filter suitable for use with the system of the present disclosure are also disclosed.

In various embodiments, the disclosed invention relates to an automated collection and filtration apparatus, and related sensor and analyzation system comprising: a collection module; a filtration module having a filter; a system of pipes and pumps; an analyzation module having an image capture device, an external processing device, and a customized AI algorithm for identifying particles captured by the image capture device.

Embodiments of the present disclosure will provide automated, real-time, in-situ concentration, collection, filtration, sorting, and analysis of target objects in open water systems.

The collection module concentrates low-density target objects for collection, allows for initial filtration not commonly found in present solutions, tracks collection data, and begins an automated pipeline by sending collected objects to the filtration module.

In the filtration module, the collected objects will pass through a calibrated filter, for example a vortex filter, filtering and pre-processing the defined target objects to be forwarded to the analyzation module where they are scanned by an image capture device and analysed by an AI algorithm loaded on an external processing device.

The term "vortex filter" as defined herein can also refer to a cyclone separator which operates under the same principles.

The AI algorithm evaluates various parameters of the objects shown in the captured image data and searches for characterising features, allowing for identification and classification of each unfiltered object.

In some embodiments, objects collected will be filtered and sorted for either storage or disposal.

Through the various technical solutions described herein embodiments of the present disclosure solve the issues arising from manual sampling techniques and allow for efficient and detailed analysis of targeted objects collected from open water systems.

In one exemplary embodiment, FIG. 1, the disclosed system comprises a collection and filtration apparatus which is integrated with an image capture and analyzation system.

The entire process is designed to be automated from the moment the objects collection begins, through the filtration, pre-processing, fluid suspension, image collection, data processing, and sorting pipeline.

In this embodiment, the system is configured to collect, filter, sort, and analyze a user-set pre-defined target object from a collected sample of water from an open water body, which may cover many different sizes, densities, and other properties and other parameters.

A collection module 110 of the system comprises a mesh screen filter 111, a trawl net 112, a water flow meter 113, and a collection box 114.

Figure 2A:
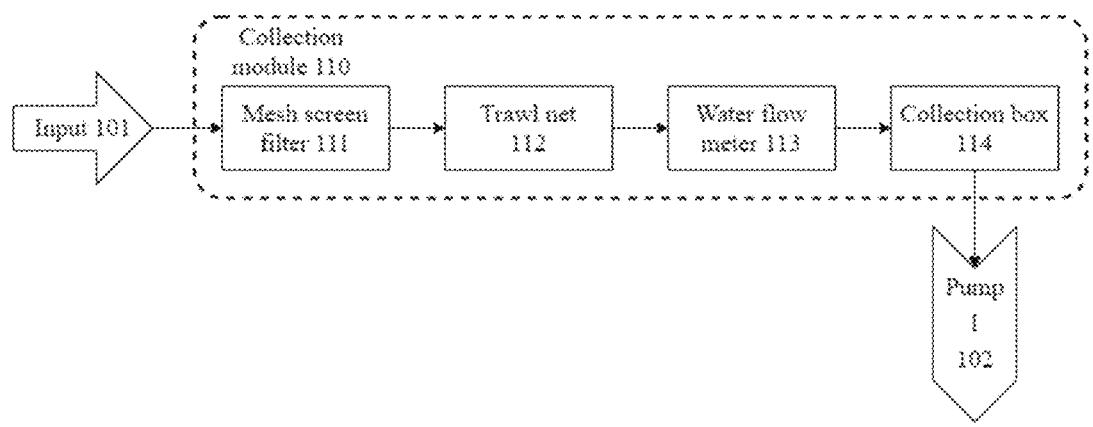
FIG. 2a is a block diagram illustrating a collection module, according to one example embodiment.

Referring to FIG. 2a the process flow of the collection module is shown isolated from the rest of the system.

Figure 2B:
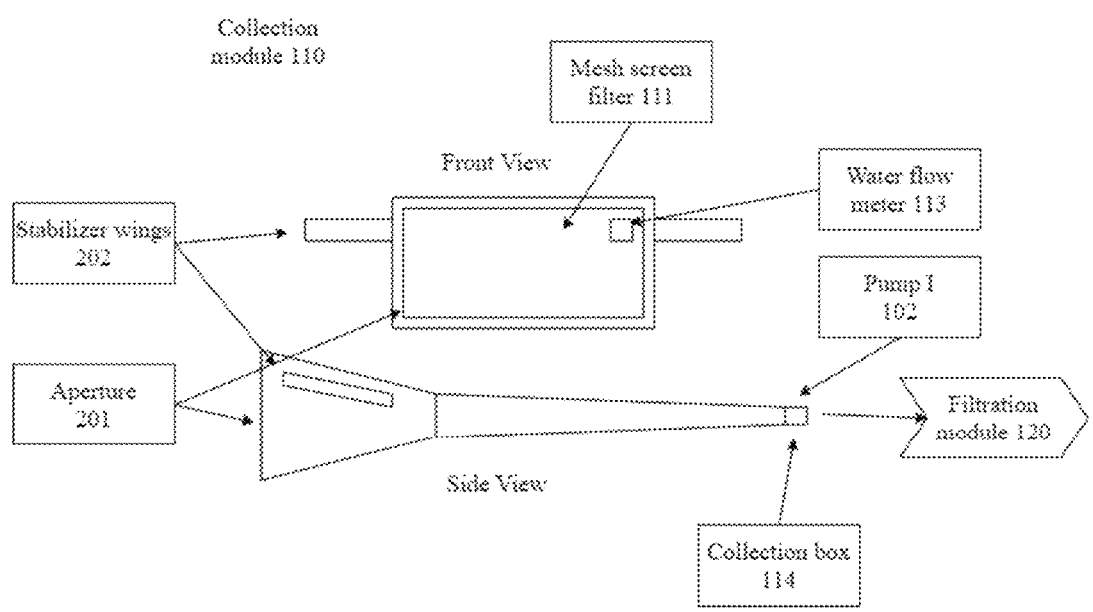
FIG. 2b is a side perspective view illustrating a collection module and a frontal perspective view illustrating a collection module with a mesh filter removed, according to one example embodiment.

FIG. 2b shows a side perspective view of the collection module, which tapers from a wide aperture 201 down to a narrow feed for collection box 114, from which particulates are pumped by pump 102 to the filtration module 120 (not illustrated).

FIG. 2b also shows a frontal perspective view of the collection module showing the mesh filter 111 covering the aperture 201.

The collection module is designed to float in an open body of water and automatically accumulate and carry out a first filtering operation on particulate matter and other objects suspended in the surrounding water as they flow past it.

To this end the module 110 comprises a mesh screen filter 111 that covers the entire wide aperture 201 of the collection module 110 and has a mesh size which is chosen to filter out objects above a predefined size threshold from the sample water that flows into the collection module from an environmental input 101, i.e. the surrounding water from the body of water in which the system is submerged. The mesh size can be varied to set an upper limit on the size of floating particulate matter that the collection module will pass to the filtration module 120.

One or more sensors may monitor the flow of water and floating particulate matter through the collection module 110, such as for example water flow meter 113. Parameters such as flow volume, velocity, and content may be monitored and forwarded to the analyzation module either for storage or for providing the AI algorithm with contextual information in identifying the target objects.

The module is further provided with stabiliser wings 202 disposed either side of the aperture 201 to maintain a steady position and orientation of the aperture 201 within the body of water. The stabiliser wings may be buoyant to offset the weight of the rest of the system and ensure the collection module floats close to the surface of a body of open water from which the samples are being collected.

The trawl net 112 forms a tapering tunnel between the aperture 201 and the collection box 114. As opposed to the mesh filter screen which filters out larger objects from entering the collection module 110, the trawl net 112 has a mesh size which is chosen to allow only objects below a predefined size threshold to escape the collection module 110. In this way, the collection apparatus can conduct initial filtration of objects, within a user-defined margin of error, for collecting the target object and objects having similar size. In some examples the meshes can also be chosen to filter out certain shapes of floating particulate matter, other parameters for filtration may also be possible.

The objects, having passed through this first filtering stage, are gathered into the collection box 114 which is located at the end of the trawl net. When a set threshold mass or volume has been reached in the collection box 114, the accumulated objects will be suspended in fluid and sent to the filtration module 120 via a system of pipelines by pump I 102. The trigger for initiating pump I 102 may be implemented in response to a signal from one or more sensors disposed within the collection box 114 and which are configured to detect when a required mass or volume of objects have accumulated there.

Referring back to FIG. 1, the objects are now flowed from collection module 110 to filtration module 120 for a second stage filtering operation by a filter 121, which may for example be a vortex filter, and are then subsequently either processed by sorting system 122 or flowed directly from an output of the filter to the analyzation module 130 by pump II 103.

Figure 3A:
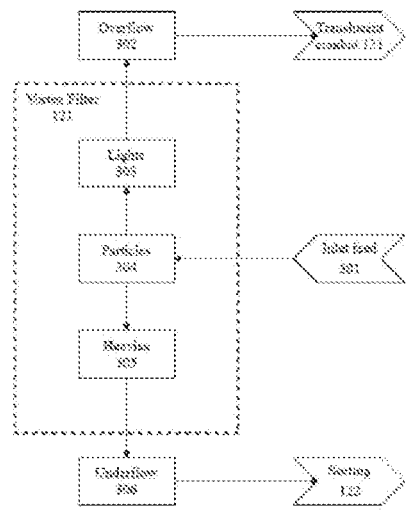
FIG. 3a is a block diagram illustrating a filtration module, according to one example embodiment.

Now turning to FIG. 3*a*, a process flow of the filtration module is shown. In the present example the filter of the filtration module is a vortex filter, however other types of filters are known to be capable of separating floating particulate matter by weight or density and could be substituted for the vortex filter 121.

In the filtration module 120, the objects are passed through vortex filter 121 via the inlet feed 301 from the pump I 102, and the filter is used to remove objects which are outside a predefined set of parameters for the target objects.

Figure 3B:
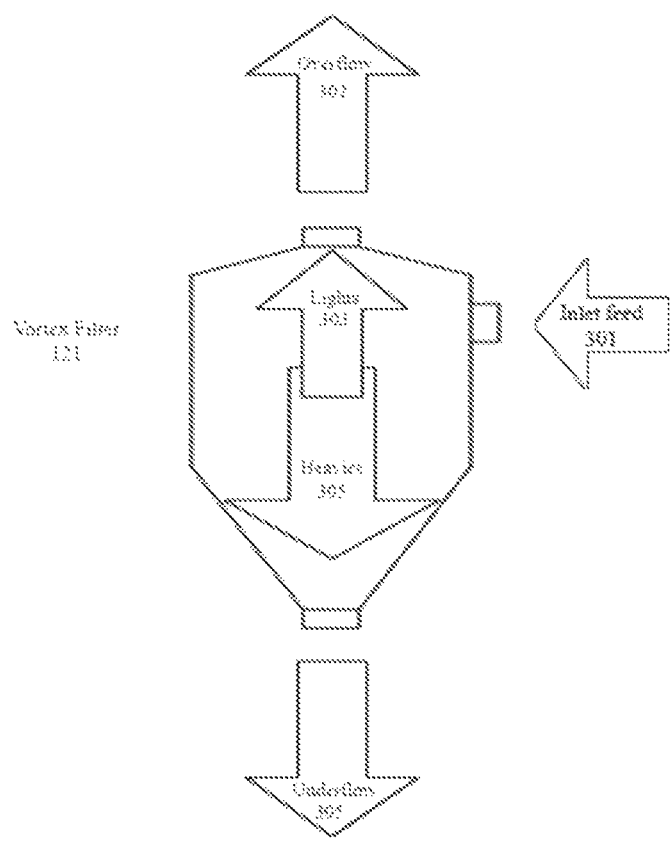
FIG. 3b is a perspective view illustrating a vortex filter and associated pump systems of the filtration module, according to one example embodiment.

In the present example, the vortex filter 121 (physically illustrated in FIG. 3*b*) will separate the floating particles 304 primarily based on density, where, as the flow from inlet feed 301 causes the water within the enclosed volume of the vortex filter to swirl, the lighter objects 303 will coalesce together and be lifted towards overflow 302 through the top section of the filter and vice versa the heavier objects 305 will coalesce in the swirl and fall downwards towards underflow 306.

In some examples, when the desired density or weight parameters are very well-defined and it is desired that the margin for error is low, a series of vortex filters 121 may be used to further filter and sort the floating particles 304.

Another aspect of the present disclosure relates to a two-stage vortex filter which effectively acts as a series of vortex filters to perform this operation, with a first stage filtering performed by a larger vortex filter that feeds into a plurality of smaller vortex filters. By controlling the ratio of the diameters of the first and second stage vortex filters and the flow speed with which the fluid sample is input into the first stage vortex filter, specific density ranges of particles can be isolated from one another. See FIGS. 6 to 8C.

The vortex filter(s) 121 serves the function of a second stage pre-processing of the collected objects prior to image capture by the analyzation module.

Referring back to FIG. 1, the lighter, unfiltered objects for analysis will be resuspended in a fluid and pumped to the analyzation module 130 by pump II 103. The path to analyzation module 130 comprises a sufficiently translucent conduit 131 for analysis (as defined by the ability of the image capture device to obtain a reasonable quality video and/or image of the objects as they pass through the conduit).

The heavier objects filtered out from the analysis (filtered objects) will be sent for sorting 122 and then to output 104. This could mean storage, disposal, or other operations, depending on the context. The objects that have passed through the translucent conduit 131 and had their image data captured may also pass to the sorting assembly 122.

Figure 3C:
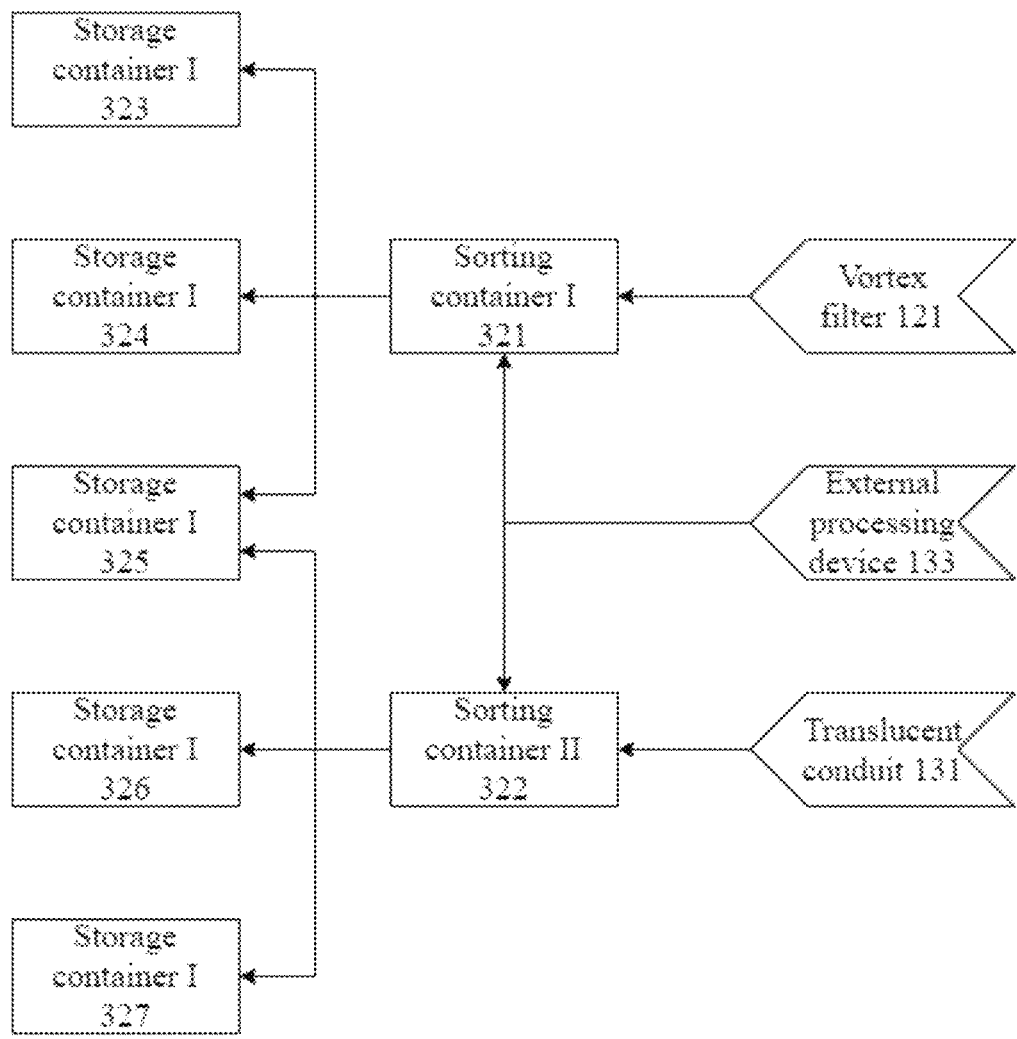
FIG. 3c is a block diagram of the post-processing sorting system for the outputs of the filtration module, according to one example embodiment.

Referring to FIG. 3*c*, an example sorting assembly 122 of the disclosed system is shown which takes outputs of both the heavy particulate matter received from vortex filter 121 and the lighter particulates run through the translucent conduit 131 of the analyzation module.

The outputs from the Vortex filter are run through a first sorting container I 321 and the outputs from the translucent conduit 131 are run through a second sorting container II 322. Both sorting containers are in the present example controlled by external processing device 133 and may comprise one or more sensors by which to detect certain parameters of the output particles and one or more valves for directing the objects to one of a plurality of storage containers. In other embodiments the sorting process may not require a processing device and may instead be entirely mechanical.

In the present example, each sorting container has access to three different storage containers, including one shared storage container 325 and two unshared storage containers. Sorting container I 321 is connected to storage container 323 and storage container 324 and sorting container II 322 is connected to storage container 326 and storage container 327. This is merely an illustrative example from any possible number of configurations for sorting and storage of the processed objects.

In other examples, the processed objects are simply flowed back into the open water environment from which they were collected.

The flow may be controlled by a series of valves and the pumps which in turn may be controlled by processing device 133. Pumps I 102 and II 103 may also be powered by the same or a different power supply.

Figure 4A:
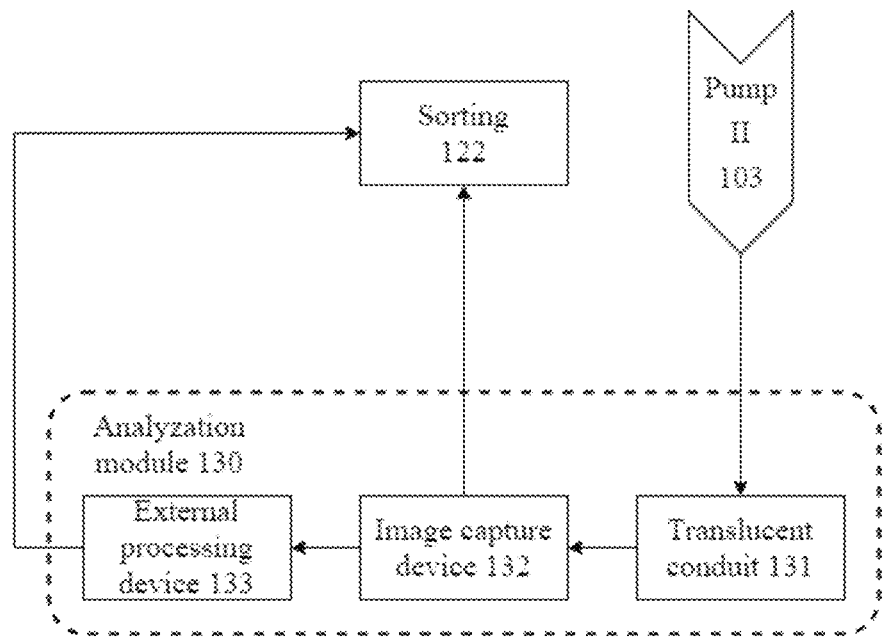
FIG. 4a is a block diagram illustrating the analyzation module, according to one example embodiment.

Referring to FIG. 4*a*, a process flow diagram of the analyzation module 130 is illustrated.

In the analyzation module 130 the unfiltered lighter objects received from the vortex filter are suspended in fluid and pumped through the translucent conduit 131 such that the image capture device 132 can capture video and/or images of the objects.

Figure 4B:
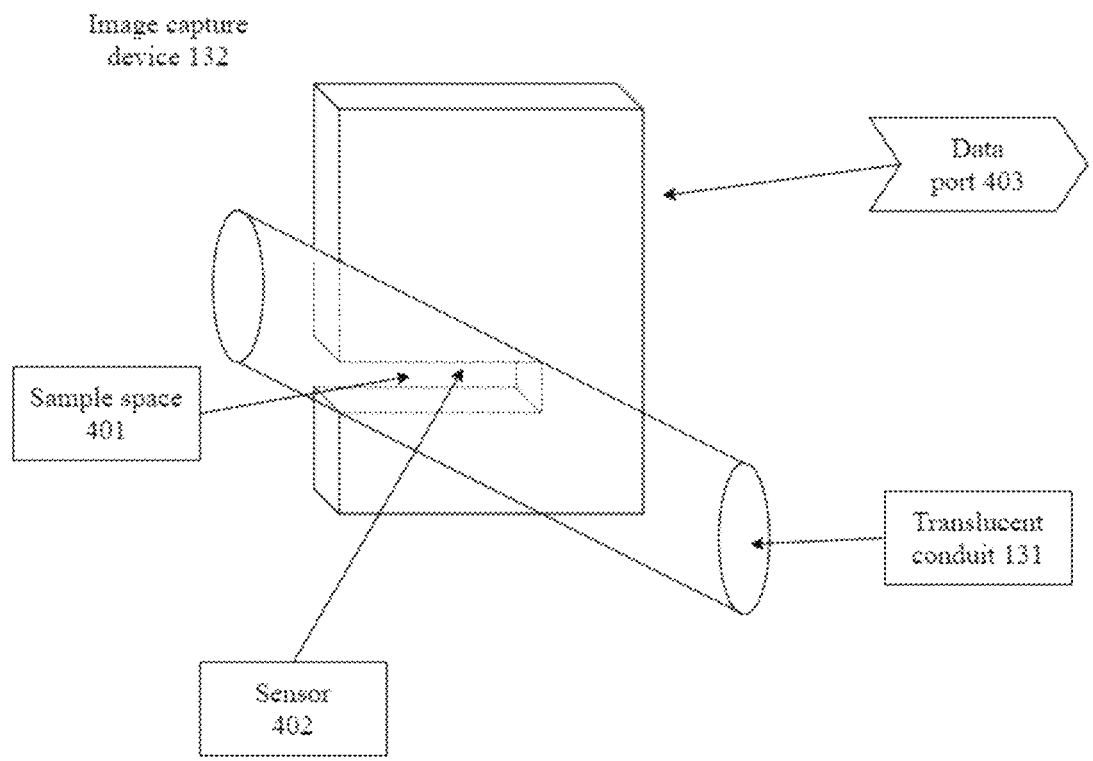
FIG. 4b is a perspective view illustrating the structure of an image capture device of the analyzation module, according to one example embodiment.

Referring to FIG. 4*b*, a simplified representation of the image capture point is shown, with translucent conduit 131 running through a sample space 401 that passes by sensor 402.

The image capture device's sensor 402 can be optical, sonar, or other, so long as video and/or images of a sufficient resolution are acquired to enable recognition and analysis of the unfiltered objects passing through. In some examples the sensor will output 3D volumetric image data based on the captured images.

The translucent conduit 131 is configured so that the unfiltered objects pass through a sample space 401 for scanning. The image data for the objects will be sent to external processing device 133 via a data port 403 on the image capture device 132. The unfiltered objects will then be sent for sorting 122 via a separate channel than the filtered objects as described above.

Since the sorting assembly and pumps and valves of the system may be controlled by the external processing device 133, in applications where it is useful to store the parsed objects, they can be separately stored in the relevant storage container of the assembly 122 based on the properties as analyzed and determined by external processing device 133.

Furthermore, in examples where the system comprises a GPS sensor, sorting the unfiltered particles may comprise associating the particles with a location of the collected sample the location determined using a GPS.

This configuration also allows for management of the flow of particulates within the device. For example the external processing device may determine to increase a speed of the pumping in response to a density of unfiltered particles at the scanning segment of the translucent tube being above a threshold value or to decrease a speed of the pumping in response to a density of unfiltered particles at the scanning segment of the translucent tube being below a threshold value.

The analysis may in some cases incorporate a machine learning model run by the external processing device 133 which is configured to determine a property of the unfiltered objects based on the captured image data. In some examples the property is selected from a texture, a size, a colour, or a shape of the unfiltered objects, or any combination thereof.

Any number of alternative or subsequent operations may also be carried out by the external processing device including but not limited to: generating a distribution chart of the property of the target objects; collecting properties of the unfiltered objects in a database of properties; uploading the collected properties to a remote computing device for dissemination; associating the one or more properties of the unfiltered particles with a certain product by comparing the unfiltered particles to particles used by the product; and training the machine learning system using a pre-determined classification.

Many suitable neural network architectures for carrying out the disclosed identification and sorting of microplastics are known, and an suitable machine learning model can be used.

The collection module 110, filtration module 120 and analyzation module 130 may be powered by a shared power supply 105.

In one use-case for the exemplary embodiment, the system is tasked to overcome disadvantages in existing solutions to microplastic particle analysis in open-water environments.

In this embodiment, the defined target objects are defined as microplastic particles less than 5.0 mm in size, and the open system an open-water environment in which the particles are floating within (defined as the top 1.0 m from the water surface down). In this embodiment, the mesh screen filter 111 has a mesh size of 5.0 mm, the trawl net 112 has a net mesh size of 335 µm, and the image capture device 132 is a holographic microscope. Furthermore, the stabiliser wings are set to a high buoyancy to keep the aperture 201 of the collection module at or above the surface of the water body as the system floats within it.

In the above embodiment, the collection module 110 collects particles from the system through the input 101 and collects particles between the sizes of 5.0 mm and 335 µm. These particles enter the collection box 114, where the collection data such as the flow of water through the aperture 201 is tracked, and the particles are suspended in fluid and sent through a pipeline by pump I 102 to the filtration module 120. In this case, suspending the particles in fluid may simply entail opening valves to allow water from the surrounding environment into the system to submerge the particles.

The particles are sent through a vortex filter 121 where particles which fall above a certain threshold density are removed. The unfiltered target particles are resuspended in fluid and pumped forward by pump II 103, and subsequently the particles are passed through a sufficiently translucent conduit 131 for the image capture device 132 to capture 3D volumetric image data of the particles as they pass through suspended in the fluid.

After image data collection the particles are sent back to the filtration module for sorting 122 and output 104, in this embodiment being storage. The 3D volumetric image data will be processed by the AI algorithm on the external processing device 133. In this embodiment, it is understood that the AI algorithm is a trained machine learning system based on a deep neural network. The machine learning system targets various properties and characteristics from the 3D volumetric image data, allowing for the system to identify which of the unfiltered particles are microplastics, and classify the type of microplastic each particle falls under. They can then be stored in an appropriate storage container after passing through sorting assembly 122.

In another use case for the exemplary embodiment, the system is tasked with observing the properties of various microorganisms suspended in an open-ocean environment. Current solutions use well-established conventional technologies, but are manual, inefficient, and cannot concentrate the different densities of the various possible target microorganisms.

Figure 5:
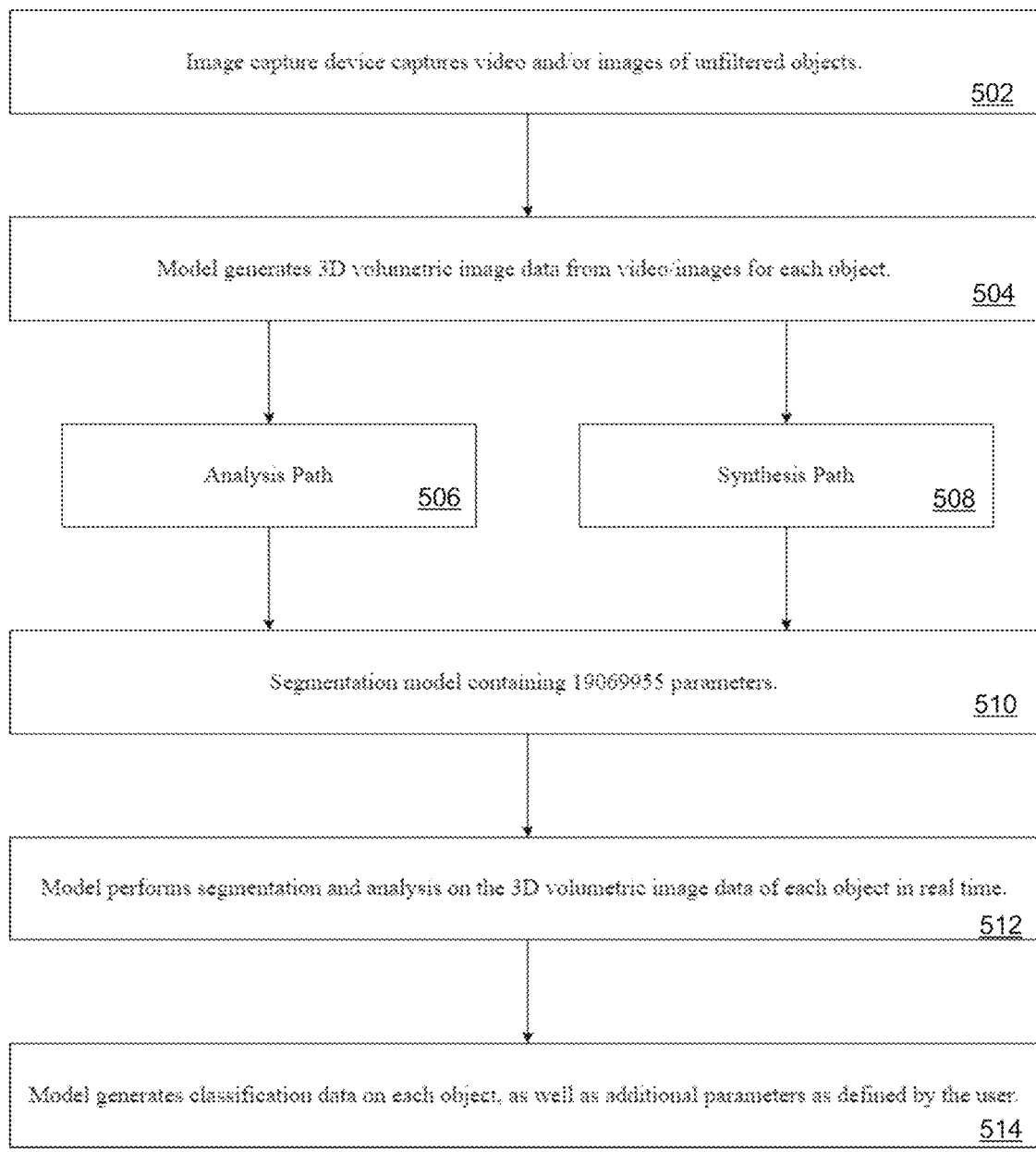
FIG. 5 is a flow diagram illustrating a method for processing image data to determine the identity and relevant properties of a target object, according to one example embodiment.

Referring to FIG. 5, a flow diagram is shown illustrating an example method for processing image data to determine the identity and relevant properties of a target object, according to one example embodiment.

In a first step 502, the method involves the image capture device capturing image data such as video or pictures of unfiltered objects passed through the analyzation module as described above.

In a second step 504, the method involves synthesising the captured image data into 3D volumetric data.

In a third step 506, the method involves a machine learning model installed on the external processing device generating 3D volumetric image data for each object based on the captured image data.

In a fourth step 508, the method involves analysing the 3D volumetric data by the processing device.

In a fifth step 510, the method involves applying a segmentation model to the processed image data, the model of the present example contains a large number of parameters.

In a sixth step 512, the model performs segmentation and analysis of the 3D volumetric data for each object in real time.

Finally in a seventh step 514, the method involves generating classification data on each object, as well as additional parameters defined by the user.

As mentioned above, a specially adapted two-stage vortex filter suitable for use with the system and methods of the present disclosure is also provided herein.

Figure 6:
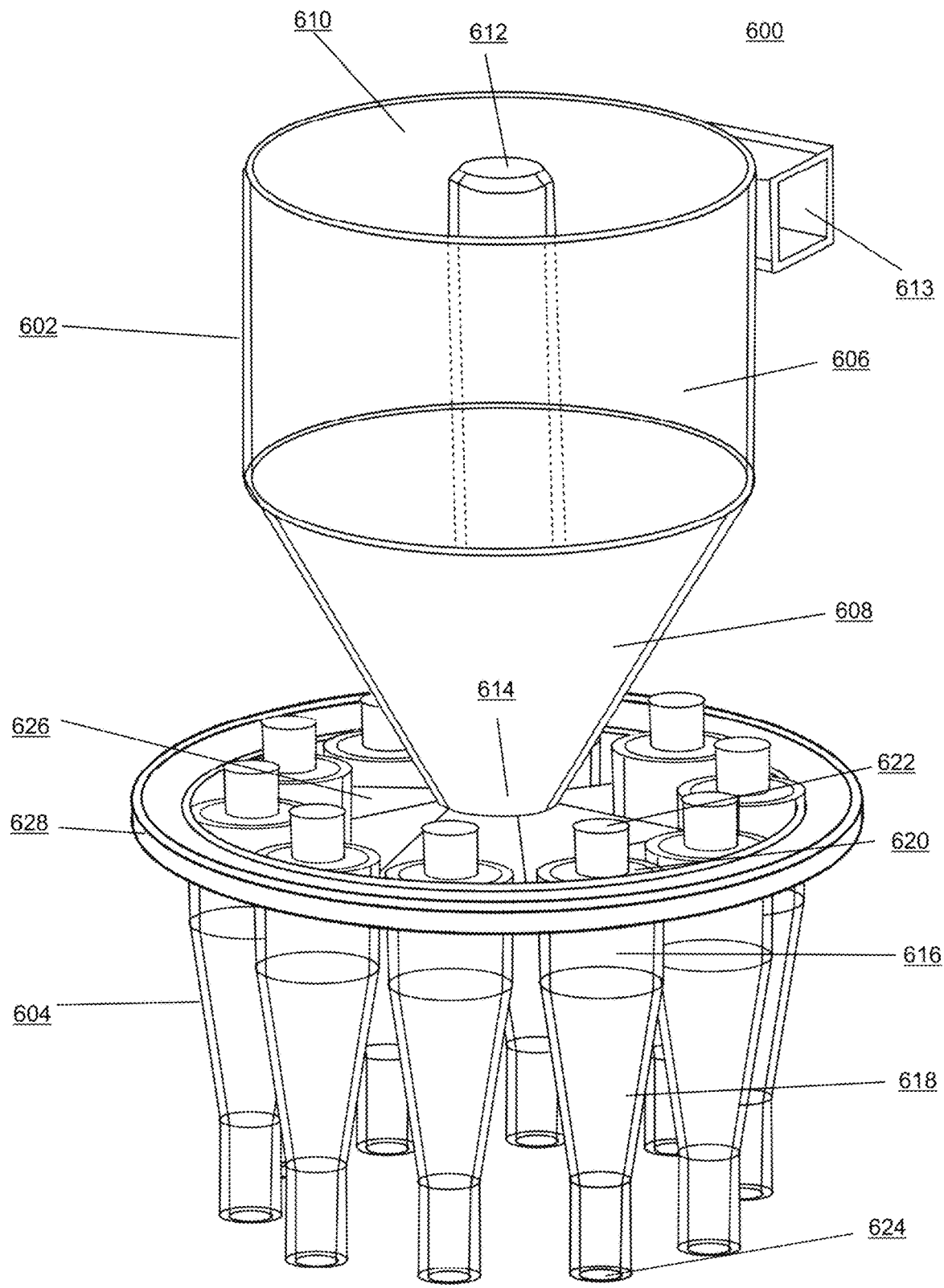
FIG. 6 illustrates an example configuration of a specially adapted vortex filter suitable for use with the disclosed open water system.
Figure 7:
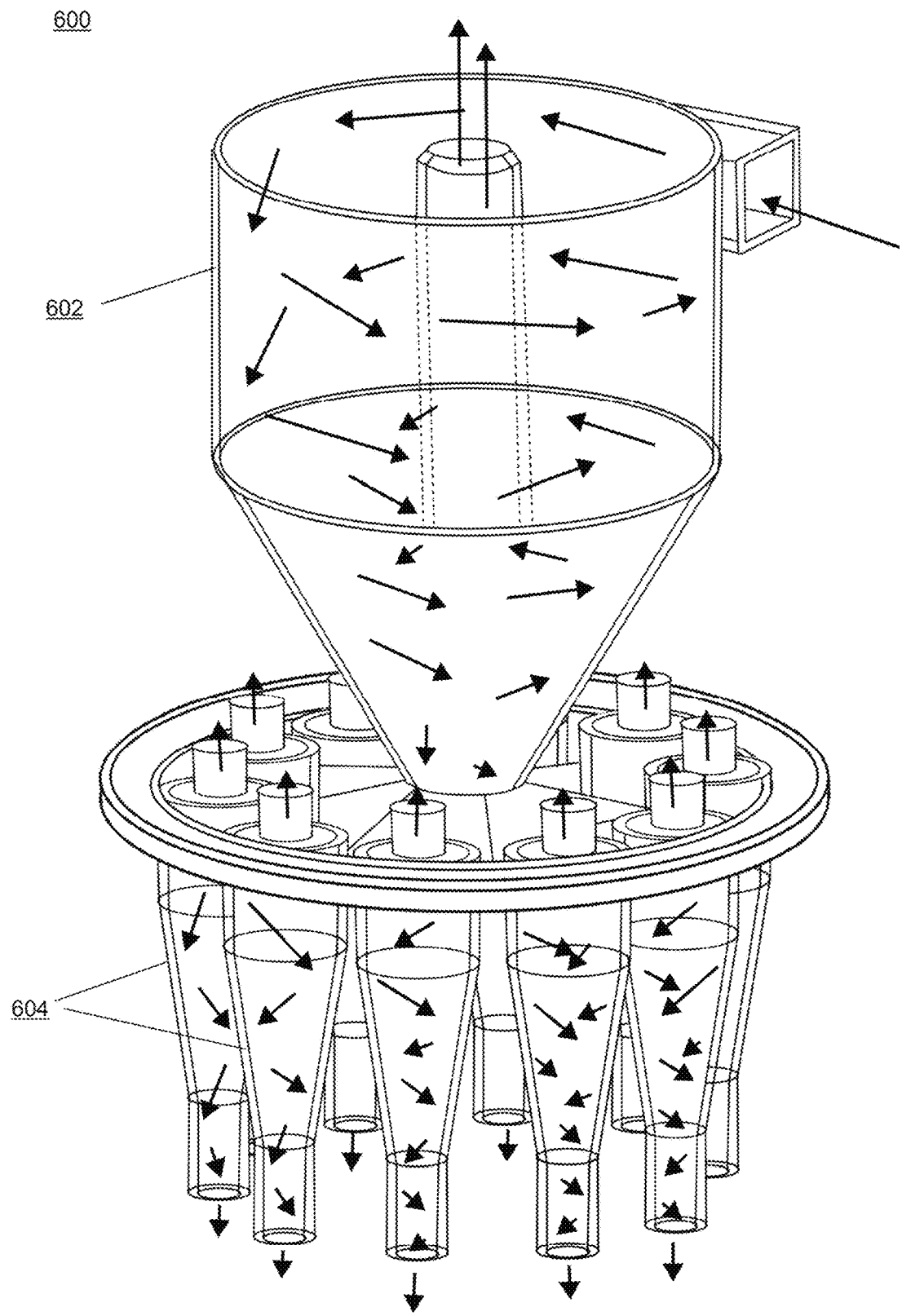
FIG. 7 illustrates the example two-stage vortex filter with a set of vectors indicating an example flow path of a fluid sample comprising floating particles within the filter.

Thus, referring to FIG. 6 and FIG. 7, an example configuration of a specially adapted vortex filter 600 is shown, both empty (FIG. 6) and with a vector field illustrating fluid flow within the filter (FIG. 7).

The filter is configured to perform first and second sorting operations of particulate matter suspended in a fluid input in order to isolate one or more objects of a desired/mass density range.

This is achieved by effectively forming an integrated series of vortex filters, a first stage large vortex filter 602 which receives the fluid input and performs a first sorting/filtering operation, and a plurality of second-stage smaller vortex filters 604 connected to the output of the first stage vortex filter that are configured to each perform a second sorting operation to isolate a more precise range of suspended particles based on their weight.

In the present example embodiment, the first stage filter 602 has a fairly standard design, with a wider cylindrical portion formed of a curved wall 606 and a tapered cone like section 608. The cylindrical section has a closed end with a lid 610 that has a central opening 612 disposed in it which acts as a first fluid outlet for light particles as will be explained below.

The sample fluid containing suspended particles for separation, for example the fluid outlet of the collection module in the open water analysis system described above, is flowed into the vortex filter 600 through fluid inlet 613. Fluid inlet 613 is aligned with the curved wall 606 of the cylindrical section of the first stage filter 602 such that once the filter is filled with fluid, the flow direction from 613 will cause new fluid input to follow the curve of the wall 606 and swirl around, creating a vortex/cyclone within.

Particles of similar mass will coalesce together, the heavier particles filtering down towards the tapered section 608 and pushing the lighter particles up, eventually causing them to exit through fluid outlet 612 (see FIG. 7), while the heavier particles sink and exit through fluid outlet 614.

This acts as a first stage filtering operation, and the range of masses of particles that will be ejected through fluid outlet 612 and fluid outlet 614 will depend directly on the velocity with which fluid is flowed into the first stage filter and the diameter of it.

The heavier particles are then directed from the fluid outlet 614 to the plurality of smaller second-stage vortex filters 604 by flow paths 626.

In the present example, each second stage filter 604 is effectively a smaller version of the first stage filter 602, with the fluid inlet receiving the particles filtered through outlet 614. Each one is oriented in the same direction as the first stage filter 602 and comprises a cylindrical portion with a curved wall 616, a tapered portion 618, a closed top part 620 with a central opening 622 that acts as a fluid outlet for lighter particles, and a central opening 624 at the end of the tapered section which acts as a fluid outlet for the heavier particles. A similar flow phenomenon can thus be observed in the second stage filters 604.

Since many smaller second stage filters 604 are used, they can handle a roughly equivalent fluid flow to the first stage filter 602, preventing bottlenecking of the filtering process. In the present example there are 10 second stage filters 604 to the one first stage filter 602, and they are banded around the output of the first stage filter in a circle, with structural reinforcement from support ring 628.

The density range of objects to be separated by the second stage filters will be determined by their diameter and the velocity with which fluid flows into them from the first stage filter.

If the very heaviest particles are desired for analysis then fluid can be collected from outputs 624, but if a range of weights is desired that has both a minimum and maximum threshold this can be achieved with precision by controlling the fluid input velocity to the first stage filter and the ratio of diameters of the first stage and second stage filters, then collecting fluid output from outputs 622.

Figure 8A:
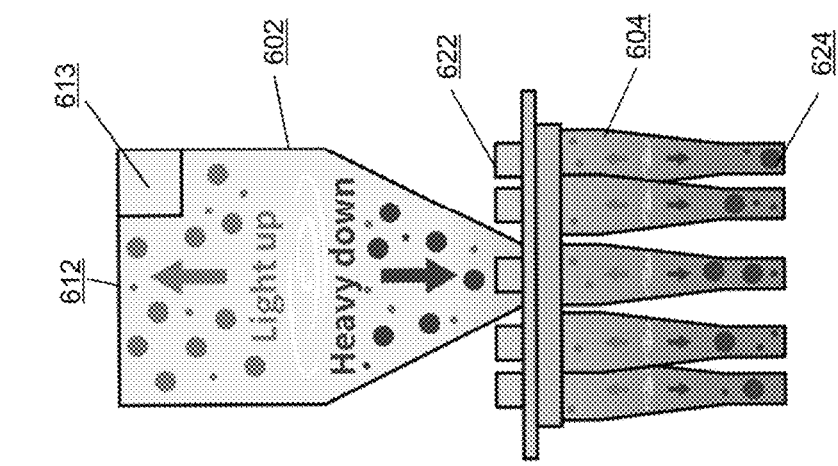
FIG. 8A to 8C illustrate a flow of the suspended particles within the two-stage filter according to their mass.
Figure 8B:
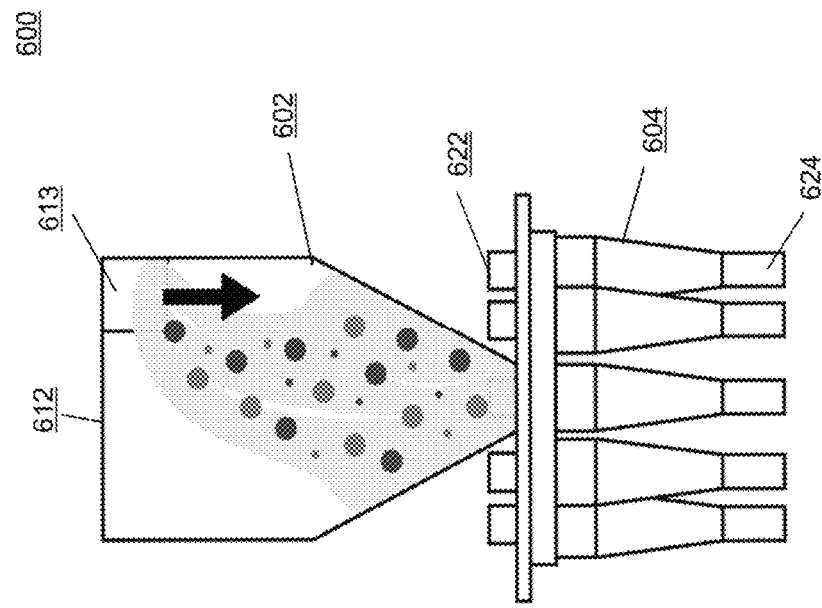
Figure 8C:
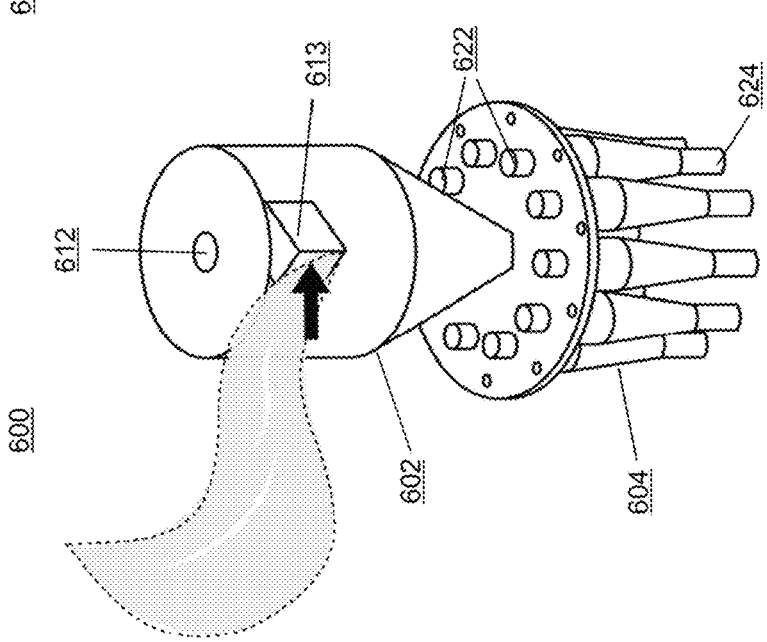

Referring to FIGS. 8A, 8B and 8C, the process of filling the filter is shown followed by the flow of the suspended particles within the two-stage filter 600 according to their mass for clarity.

In FIG. 8A the first fluid input is flowed into the first stage filter 602. In FIG. 8B the first stage filter 602 is still being filled with fluid and so the arrangement of the suspended particles is still disordered. In FIG. 8C both stages of filters have been filled and the suspended particles have begun to filter with the heavier particles sinking and the lighter particles rising.

Unless otherwise defined, all terms (including technical terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

The disclosed embodiments are illustrative, not restrictive. While specific configurations of the open water analysis system and vortex filter have been described in a specific manner referring to the illustrated embodiments, it is understood that the present invention can be applied to a wide variety of solutions which fit within the scope and spirit of the claims. There are many alternative ways of implementing the invention.

It is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A system for collecting and analysing samples from an open water environment, the system comprising:
   a collection module configured to float within and receive water samples from a surrounding open water environment, the collection module comprising one or more filters for collecting objects of a target size range from the water samples;
   a filtration module comprising a filter configured to separate the collected objects according to a predetermined parameter and comprising outputs for the filtered and unfiltered objects;
   an analyzation module comprising an imaging device and a processing device, the analyzation module configured to image the unfiltered objects from the filtration module to determine one or more characteristics of parameters of the unfiltered objects,
   whereby the collection module, the filtration module and the analyzation module are operatively connected together to collect and analyze samples from the open water environment.

2. A system according to claim 1, wherein the analysation module comprising a translucent tube configured to pass the unfiltered objects through a scanning area of the imaging device.

3. A system according to claim 2, wherein the filtration module further comprises a sorting assembly configured to receive any or a combination of an output of the filter and an output of the imaging device.

4. A system according to claim 3, wherein the sorting assembly comprises one or more storage containers and one or more valves for directing the received filtered and unfiltered objects into the storage containers.

5. A system according to claim 4, wherein the unfiltered objects are sorted according to one or more parameters or characteristics determined by the analyzation module.

6. A system according to claim 1, wherein the image capture device is configured to generate 3D volumetric data for the unfiltered objects.

7. A system according to claim 1, wherein the processing device is configured to classify and/or identify the unfiltered objects based on the image data captured by the image capture device.

8. A system according to claim 6, wherein the processing device comprising a machine learning algorithm for classifying or identifying the unfiltered objects based on the captured image data.

9. A system according to claim 1, wherein the system comprises an assembly of pumps and valves for directing the captured objects through the system.

10. A system according to claim 1, wherein the collection module comprises a mesh filter at an input aperture for preventing objects above a certain size from entering the filter.

11. A system according to claim 10, wherein the collection module comprises a trawl net between the mesh filter and a collection box for receiving the objects, the trawl net having a mesh size chosen to allow objects below a certain size to escape the collection module.

12. A system according to claim 1, wherein the collection module is provided with one or more buoyant stabilisers for maintaining a desired depth and/or orientation of the collection module.

13. A system according to claim 1, wherein filter of the filtration module is a vortex filter configured to filter the objects by density.

\* \* \* \* \*